(12) United States Patent
Malone et al.

(10) Patent No.: US 7,223,415 B1
(45) Date of Patent: May 29, 2007

(54) WEATHER RESISTANT GRANULAR BAIT WITH SYNERGISTIC BROAD SPECTRUM ATTRACTANT SYSTEM

(75) Inventors: Tracy D. Malone, Knoxville, TN (US); Ronald T. Schwalb, Knoxville, TN (US); Kevin L. Kirkland, Knoxville, TN (US)

(73) Assignee: Nisus Corporation, Rockford, TN (US)

( * ) Notice: Subject to any disclaimer, the term of this patent is extended or adjusted under 35 U.S.C. 154(b) by 0 days.

(21) Appl. No.: 10/266,191

(22) Filed: Oct. 7, 2002

(51) Int. Cl.
*A01N 25/32* (2006.01)

(52) U.S. Cl. .................... 424/406; 424/84; 424/408; 424/405; 424/417; 424/658; 424/659; 424/660

(58) Field of Classification Search ............. 424/405, 424/406, 408, 417, 84
See application file for complete search history.

(56) References Cited

U.S. PATENT DOCUMENTS

| | | | |
|---|---|---|---|
| 4,826,682 A | | 5/1989 | Sakharova |
| 4,996,053 A | | 2/1991 | Hatcher |
| 5,096,710 A | * | 3/1992 | Minagawa et al. ......... 424/405 |
| 5,223,270 A | | 6/1993 | Jones |
| 5,273,761 A | | 12/1993 | Kim et al. |
| 5,665,370 A | | 9/1997 | Gehret et al. |
| 5,676,961 A | | 10/1997 | Wolfe et al. |
| 5,705,176 A | | 1/1998 | Stapleton et al. |
| 5,820,855 A | | 10/1998 | Barcay et al. |
| 5,885,606 A | | 3/1999 | Kawada |
| 5,939,061 A | | 8/1999 | Vail et al. |
| 6,007,832 A | | 12/1999 | Stapleton |
| 6,153,181 A | | 11/2000 | Nelson et al. |
| 6,352,693 B1 | | 3/2002 | Kawada |
| 6,369,078 B1 | | 4/2002 | Bowen et al. |
| 6,645,949 B1 | | 11/2003 | Nigg et al. |
| 6,773,727 B1 | * | 8/2004 | Rojas et al. ............. 424/725 |
| 2002/0010156 A1 | | 1/2002 | Kennedy et al. |

FOREIGN PATENT DOCUMENTS

| | | |
|---|---|---|
| AU | 9667961 A | 4/1997 |
| AU | 2003 203 735 A1 | 4/2003 |
| BE | 755598 A | 9/1970 |
| CN | 1123088 A | 5/1996 |
| CN | 1129066 A | 8/1996 |
| DE | 2431595 | 1/1976 |
| DE | 298584 A5 | 3/1992 |
| DE | 19622513 A1 | 12/1997 |
| DE | 101 32 532 A1 | 2/2003 |
| EP | 0 248 991 | 12/1987 |
| EP | 0 246 477 B1 | 6/1990 |
| FR | 2491296 A | 4/1982 |
| GB | 2271579 A | 4/1994 |
| JP | 48033019 A | 5/1973 |
| JP | 50135234 A | 10/1975 |
| JP | 62195301 | 8/1987 |
| JP | 2111702 A | 4/1990 |
| JP | 2169505 A | 6/1990 |
| JP | 2223501 A | 9/1990 |
| JP | 2262501 A | 10/1990 |
| JP | 8133917 A | 5/1996 |
| JP | 9131154 A | 5/1997 |
| KR | 9509506 B1 | 8/1995 |
| KR | 2000066482 A | 11/2000 |
| WO | WO 92/22205 | 12/1992 |
| WO | WO 95/35029 | 12/1995 |
| WO | WO 99/43476 | 9/1999 |
| WO | WO 00/11948 | 3/2000 |
| WO | WO 00/15033 | 3/2000 |
| WO | WO 01/17348 A1 | 3/2001 |
| WO | WO 01/87559 A2 | 11/2001 |
| WO | WO 02/06417 | 1/2002 |
| WO | WO 02/06417 A1 | 1/2002 |
| ZA | 8004816 A | 4/1981 |
| ZA | 9002080 A | 11/1990 |

OTHER PUBLICATIONS

Lloyd, S. N., "NiBan Weather Testing Report," Nisus Corporation (2002).
Rykov, R.I., "Reaction of preserved woods with adhesive hardeners," Tr. Mezhvuz. Kong. Primen. Plastmass Stroit., (3rd) (1972) Meeting Date 1970, 157-8 (Abstract).
Trek et al., "Protection of oriented strandboard with borate," Forest Products Journal 49(6), 47-51 (1999) (Abstract).
Cardoza, Ron "Laboratory Evaluation of Niban® Granular Bait in the control of Pavement Ants," Bio Study No. 134-02, pp. 1-9.
Cardoza, Ron "Laboratory Evaluation of Niban® Granular Bait in the control of Southern Fire Ants," Bio Study No. 147-02, pp. 1-13.
Cardoza, Ron "Laboratory Evaluation Of Niban® Granular Bait in the control of Argentine Ants," Bio Study No. 252-02. pp. 1-8.

* cited by examiner

*Primary Examiner*—Neil S. Levy
(74) *Attorney, Agent, or Firm*—Luedeka, Neely & Graham, P.C.

(57) ABSTRACT

Weather resistant granular baits containing an attractant system are disclosed. Methods of making and using the baits are also disclosed.

18 Claims, No Drawings

WEATHER RESISTANT GRANULAR BAIT WITH SYNERGISTIC BROAD SPECTRUM ATTRACTANT SYSTEM

FIELD OF THE INVENTION

The present invention is directed to baits containing an attractant system. The present invention is further directed to methods of making and using the baits.

BACKGROUND OF THE INVENTION

Borates have been used as an effective, low acute mammalian toxicity, non-resistance generating pesticide for the control of ants, cockroaches, and other insects for decades. Borate products have been commercially available in solid, granular form or in liquid form.

Many conventional borate-containing pesticides have one or more shortcomings.

SUMMARY OF THE INVENTION

The present invention provides granular bait compositions that desirably possess one or more of the following properties: desired weather resistance, desired UV light resistance, desired heat resistance, or the ability to provide effective pesticidal treatment for a variety of insects. The granular baits contain at least one pesticidally active ingredient, at least one carrier material, and an attractant system comprising at least two attractants. In one exemplary embodiment of the present invention, the attractant system comprises powdered sugar in combination with corn oil.

The present invention is further directed to a method of making granular bait comprising a number of method steps. In one exemplary embodiment of the present invention, granular bait is prepared using a dry method, wherein the method comprises (i) forming a dry mixture of (a) an effective amount of at least one pesticidally active ingredient, (b) one or more carrier materials, wherein at least one carrier material is corncob grit, and (c) a first attractant, wherein the first attractant is powdered sugar; and (ii) adding a second attractant to the dry mixture while mixing to form particulate material, wherein the second attractant is corn oil. One pesticidally active ingredient suitable for use in the present invention is orthoboric acid.

The present invention is also directed to a method of making granular bait using a wet method. One exemplary method comprises (i) forming a dry mixture of (a) an effective amount of at least one pesticidally active ingredient, (b) one or more carrier materials, wherein at least one carrier material is corncob grit, and (c) a first attractant, wherein the first attractant is powdered sugar; (ii) adding a second attractant to the dry mixture, wherein the second attractant is corn oil; (iii) adding water and at least one additional carrier material selected from agar and gelatin to the dry mixture to form a moldable slurry; and (iv) applying heat to the slurry to form moldable material. In a further embodiment, the moldable material may be shaped by a shaping step, such as an extrusion step.

The present invention is further directed to a method of controlling one or more insect pests in an area by applying granular bait to at least a portion of the area. The methods may be used to control a variety of arthropods including, but not limited to, cockroaches, silverfish, crickets, and numerous species of ants in a single application.

These and other features and advantages of the present invention will become apparent after a review of the following detailed description of the disclosed embodiments and the appended claims.

DETAILED DESCRIPTION OF THE INVENTION

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

The present invention is directed to a granular bait composition, which provides effective control of a broad range of insects. The present invention is further directed to a method of controlling one or more insect pests in an area by applying granular bait to at least a portion of the area. In addition, the present invention is directed to a method of making granular bait.

I. Granular Bait
  A. Composition
  The granular bait of the present invention comprises one or more of the following composition components.
    1. Pesticidally Active Ingredient
    The granular bait of the present invention comprises an effective amount of at least one pesticidally active ingredient. Suitable pesticidally active ingredients for use in the present invention include, but are not limited to, boric acid; orthoboric acid; sodium borates such as borax, disodium octaborate, and sodium pentaborate; sodium calcium borates such as ulexite; sodium magnesium borates such as hydroboracite; and calcium borates such as colemanite; and combinations thereof. Desirably, the granular bait of the present invention comprises boric acid or orthoboric acid.

As used herein, the term "effective amount" refers to an amount, which provides a desired degree of control over one or more insect pests such that the one or more insect pests (a) leave a given area of application, and/or (b) consume the granular bait resulting in the death or incapacitation of the one or more insect pests. Typically, the at least one pesticidally active ingredient is present in the granular bait in an effective amount ranging from greater than 0 to about 10 percent by weight (pbw) based on a total weight of the granular bait. Desirably, the at least one pesticidally active ingredient is present in the granular bait in an amount ranging from about 0.5 to about 6.0 pbw based on a total weight of the granular bait. More desirably, the at least one pesticidally active ingredient is present in the granular bait in an amount ranging from about 4.0 to about 6.0 pbw based on a total weight of the granular bait.

In one desired embodiment of the present invention, the granular bait comprises about 5.0 pbw of boric acid based on a total weight of the granular bait. Boric acid is commercially available from U.S. Borax, Inc. (Wilmington, Calif.) as a powder having an average particle size of about 200 microns to 300 microns and sold under the trade designation Optibor TG or Boric Acid MG.

2. Carrier Materials
    The granular bait of the present invention also comprises one or more carrier materials. Suitable carrier materials for use in the present invention include, but are not limited to, corncob grit; ground soy bean hulls; granular agricultural by-products, i.e. seeds, shells, hulls, or husks; and combinations thereof. Desirably, the at least one carrier material is corncob grit. Suitable corncob grit for use in the present invention includes, but is not limited to, commercially available corncob grit from Independence Corn By Products (Independence, Iowa) as a particulate material having an average particle size of about 800 microns and sold under the trade designation CG 14-40 or 1060 DZ.

Typically, the one or more carrier materials are present in the granular bait in an amount ranging from about 50 to about 90 pbw based on a total weight of the granular bait, Desirably, the one or more carrier materials are present in the granular bait in an amount ranging from about 60.0 to about 80.0 pbw based on a total weight of the granular bait. More desirably, the one or more carrier materials are present in the granular bait in an amount ranging from about 65.0 to about 75.0 pbw based on a total weight of the granular bait.

In one desired embodiment of the present invention, the granular bait comprises about 70.0 pbw of one or more carrier materials based on a total weight of the granular bait, wherein the one or more carrier materials comprise corncob grit.

Suitable ground soy bean hulls and granular agricultural by-products, i.e. seeds, shells, hulls, or husks, for use in the present invention are commercially available from a variety of vendors including, but not limited to, Tennessee Farmers Cooperative (Lavergne, Tenn.).

Other carrier materials, in addition to the corncob grit, ground soybean hulls, and granular agricultural by-products described above, may be present in the granular bait of the present invention. Other suitable carrier materials include, but are not limited to, agar, gelatin, or a combination thereof, Suitable agar for use in the present invention is commercially available from Becton Dickinson and Company (Sparks, Md.) as a particulate material having an average particle size of about 200 microns and sold under the trade designation Agar Technical. Suitable gelatin for use in the present invention is commercially available from Becton Dickinson and Company (Sparks, Md.) as a particulate material having an average particle size of about 800 microns and sold under the trade designation Gelatin. When present, the other carrier materials comprise up to about 2.0 pbw based on a total weight of the granular bait.

3. Attractant System

The granular bait of the present invention further comprises an attractant system comprising at least two attractants. The first attractant comprises an attractant selected from the group consisting of powdered sugar, granulated sugar, dextrose, sucrose, fructose, sugar-containing food by-products composed of at least 60 wt % sugar by analysis (e.g., TAST-E-BAIT®, available from Advanced Organics, Sandusky, Ohio), or a combination thereof. The second attractant comprises an attractant selected from the group consisting of corn oil, soy oil, vegetable oil, or oil-containing food by-products composed of 10 wt % food-grade oils by analysis (e.g., TAST-E-BAIT®), or a combination thereof. Desirably, the first attractant is powdered sugar (i.e., 97 wt % sucrose, 3 wt % corn starch) (also known as confectioner's sugar) and the second attractant is corn oil. More desirably, the first attractant is powdered, confectioner's sugar having a particle size of 6× to 12×.

Suitable powdered sugar for use in the present invention is commercially available from Domino Foods (Arabi, La.) as a particulate material having an average particle size of about 75 microns and sold under the trade designation Confectioner's Sugar 10×. Suitable corn oil for use in the present invention is commercially available from Cargill Foods (Memphis, Tenn.) as a liquid material having a viscosity of about 250 centipoises and sold under the trade designation RB Corn Oil.

Typically, the first attractant is present in the granular bait in an amount ranging from greater than 0 to about 20.0 pbw based on a total weight of the granular bait. Desirably, the first attractant is present in the granular bait in an amount ranging from about 5.0 to about 15.0 pbw based on a total weight of the granular bait. More desirably, the first attractant is present in the granular bait in an amount ranging from about 8.0 to about 12.0 pbw based on a total weight of the granular bait.

Typically, the second attractant is present in the granular bait in an amount ranging from greater than 0 to about 30.0 pbw based on a total weight of the granular bait. Desirably, the second attractant is present in the granular bait in an amount ranging from about 10.0 to about 20.0 pbw based on a total weight of the granular bait. More desirably, the second attractant is present in the granular bait in an amount ranging from about 12.0 to about 18.0 pbw based on a total weight of the granular bait.

In one desired embodiment of the present invention, the granular bait comprises about 10 percent by weight of a first attractant in the form of powdered sugar, and about 15 percent by weight of a second attractant in the form of corn oil based on a total weight of the granular bait.

A variety of suitable first attractants other than powdered sugar, such as granulated sugar, dextrose, sucrose, fructose, and sugar-containing food by-products, are commercially available from a number of sources, any of which may be used in the present invention. Like the first attractants, a variety of suitable second attractants other than corn oil, such as soy oil, vegetable oil, or oil-containing food by-products, are commercially available from a number of sources, any of which may be used in the present invention.

Other attractants, in addition to the first and second attractants described above, may be present in the granular bait of the present invention. Other suitable attractants include, but are not limited to, protein sources such as yeast extract, soy, albumin, and carbohydrate sources such as wheat, corn, oat, rice or potato flour, malt extract, food by-products, or a combination thereof. When present, the other attractants comprise up to about 25.0 pbw of the granular bait based on a total weight of the granular bait.

4. Optional Additives

The granular bait of the present invention may further comprise one or more optional additives. Suitable optional additives include, but are not limited to, colorants, marking agents, tracers, fillers, desiccants, deodorizers, preservatives, and combinations thereof. When present, the optional additives comprise up to about 5.0 pbw of the granular bait based on a total weight of the granular bait.

B. Granular Bait Structure

The granular bait of the present invention typically comprises a plurality of granular bait particles having a given shape and a desired average particle size ranging from about 400 microns to about 1000 microns. The particles may have a particular shape, which varies depending on a number of factors including, but not limited to, the components used, and the process steps used to produce the particles. The particle shape is typically unsymmetrical, having a spherical, cubical, rectangular, or rod-like shape.

The particles may have a selected particle size, which varies depending on a number of factors including, but not limited to, the targeted insect or insects, the components used, the processibility of the components used, and the application method.

In one desired embodiment of the present invention, the granular bait comprises a plurality of particles, wherein the plurality of particles pass through a #8 mesh screen, but do not pass through a #100 mesh screen. This corresponds roughly to particles having a particle diameter ranging from about 150 microns (μm) to about 2500 μm. (As used herein, the term "particle diameter" is used to describe at least one cross-sectional dimension of the particle. For example, if the particles are rod-shaped particles, the particle diameter may represent the length or the width of the particle.) More desirably, the granular bait comprises a plurality of particles, wherein the plurality of particles pass through a #14 mesh screen, but do not pass through a #80 mesh screen. This corresponds roughly to particles having a particle diameter ranging from about 160 μm to about 1100 μm.

Typically, the granular bait comprises a plurality of particles, wherein a majority of the particles have a substantially uniform composition distributed across the particle surface area. In other words, the composition components are uniformly distributed across the particle surface area.

II. Method of Making Granular Baits

The present invention is further directed to methods of making granular baits. In one exemplary embodiment of the present invention, granular bait is prepared using a method, wherein the method comprises (i) forming a dry mixture of (a) an effective amount of at least one pesticidally active ingredient, (b) one or more carrier materials, wherein at least one carrier material is corncob grit, ground soy bean hulls, or granular agricultural by-products, i.e. seeds, shells, hulls, or husks, and (c) a first attractant, wherein the first attractant is powdered sugar, granulated sugar, dextrose, sucrose, fructose, sugar-containing food by-products, or a combination there of; and (ii) adding a second attractant to the dry mixture while mixing to form particulate material, wherein the second attractant is corn oil, soy oil, vegetable oil, or oil-containing food by-products, or a combination thereof. Desirably, the at least one pesticidally active ingredient comprises boric acid.

In a further embodiment of the present invention, granular bait is prepared using a wet method, wherein the method comprises the above steps and the following steps: (iii) adding water and at least one additional carrier material selected from agar and gelatin to the dry mixture to form a moldable slurry; and (iv) applying heat to the slurry to remove water. In this embodiment, the moldable slurry may be shaped by one or more shaping steps to form shaped objects. Suitable shaping steps include, but are not limited to, an extrusion step.

The above methods may further include a screening step, the particulate granular bait material is screened to provide a plurality of particles that pass through a #8 mesh screen, but do not pass through a #100 mesh screen. As discussed above, this corresponds roughly to particles having a particle diameter ranging from about 150 μm to about 2500 μm. More desirably, the particulate granular bait material is screened to provide a plurality of particles, wherein the plurality of particles pass through a #14 mesh screen, but do not pass through a #80 mesh screen (i.e., particles having a particle diameter ranging from about 160 μm to about 100 μm).

III. Methods of Applying Granular Bait to an Area

The present invention is even further directed to methods of applying granular bait to an area. In one embodiment of the present invention, a method of reducing the number of insect pests in an area comprises applying or distributing a granular bait to at least a portion of the area, wherein the granular bait comprises one or more granular bait compositions described above.

The method may be used to control a variety of insects including, but not limited to, cockroaches; silverfish; crickets; and numerous species of ants including fire ants, Argentine ants, odorous house ants, carpenter ants, and pavement ants. One exemplary method comprises treating an exterior perimeter of a structure in a band having a bandwidth of from about 2 to about 4 feet wide at a distribution rate of about 6 ounces per 100 square feet. The bait may be distributed by a broadcasting device (i.e., bait or fertilizer spreader), by hand, by using baiting trays, or by using bait stations. Another exemplary exterior application method comprises applying bait at a distribution rate of about 90 pounds per acre using a powered mechanical spreader. An exemplary method for treating an interior of a structure comprise spreading the bait in cracks, crevices, and crawlspaces by hand or by baiting trays or bait stations at a distribution rate of about 6 ounces per 100 square feet.

IV. Specific Exemplary Embodiments

In one desired embodiment of the present invention, the granular bait comprises (a) boric acid; (b) corncob grit; (c) powdered sugar; and (d) corn oil. Desirably, the granular bait comprises (a) from greater than 0 to about 10 pbw of boric acid; (b) from about 50 to about 90 pbw of corncob grit; (c) from about 5 to about 15 pbw of powdered sugar; and (d) from about 10 to about 20 pbw of corn oil, wherein all percents by weight are based on a total weight of the granular bait.

In a further desired embodiment of the present invention, the granular bait consists essentially of (a) boric acid; (b) corncob grit; (c) powdered sugar; and (d) corn oil, wherein the granular bait may further contain an optional filler. Desirably, the granular bait consists essentially of (a) from greater than 0 to about 10 pbw of boric acid; (b) from about 50 to about 90 pbw of corncob grit; (c) from about 5 to about 15 pbw of powdered sugar; and (d) from about 10 to about 20 pbw of corn oil, wherein all percents by weight are based on a total weight of the granular bait.

In yet a further embodiment of the present invention, the granular bait consists of (a) boric acid; (b) corncob grit; (c) powdered sugar; and (d) corn oil. Desirably, the granular bait consists of (a) from greater than 0 to about 10 pbw of boric acid; (b) from about 50 to about 90 pbw of corncob grit; (c) from about 5 to about 15 pbw of powdered sugar; and (d) from about 10 to about 20 pbw of corn oil, wherein all percents by weight are based on a total weight of the granular bait. More desirably, the granular bait consists of (a) about 5 pbw of boric acid; (b) about 70 pbw of corncob grit; (c) about 10 pbw of powdered sugar; and (d) about 15 pbw of corn oil, wherein all percents by weight are based on a total weight of the granular bait.

In each of the above embodiments, the granular bait is desirably substantially water-free. Although a water content up to about 5.0 pbw does not negatively impact the structural integrity of the granular bait, it is desirable for packaging purposes, storage purposes, and application purposes to minimize the water content of the granular bait.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Preparation of Granular Bait

Granular bait was prepared by premixing the following components in a Marion mixer ribbon blender, Model No. BPC-4296 available from Marion, Inc. (Marion, Iowa) for about 5 to 10 minutes: (a) boric acid commercially available from U.S. Borax, Inc. (Wilmington, Calif.) under the trade designation Optibor TG; (b) corncob grit commercially available from Independence Corn By Products (Independence, Iowa) under the trade designation CG 14-40; and (c) powdered sugar commercially available from Domino Foods (Arabi, La.) under the trade designation Confectioner's Sugar 10×. Corn oil commercially available from Cargill Foods (Memphis, Tenn.) under the trade designation RB Corn Oil was added to the mixture. The mixture was mixed for an additional 20 to 25 minutes.

The resulting granules had an overall composition of:

| boric acid | 5 pbw |
| corncob grit | 70 pbw |
| powdered sugar | 10 pbw |
| corn oil | 15 pbw |

The granules were screened to obtain a plurality of particles having a particle size ranging from about 160 μm to about 1100 μm.

EXAMPLE 2

Preparation of Granular Bait Using a Shaping Step

Granular bait was prepared using a wet method. The following components were pre-mixed for about 5 to 10 minutes using the equipment and procedure of Example 1: (a) Optibor TG boric acid; (b) CG 14-40 corncob grit; (c) Confectioner's Sugar 10× powdered sugar; and (d) RB Corn Oil. Water was then added to the mixture along with agar commercially available from Becton Dickinson and Company (Sparks, Md.) under the trade designation Agar Technical to form a moldable slurry. The slurry was mixed for an additional 20 to 25 minutes, and then extruded through a heated extruder commercially available from Akron Corporation (Akron, Ohio), Model No. 6024V. During the extrusion step, melting of the agar occurred, and upon cooling, the product could be formed to fit in molds of any required shape or size.

The resulting shapes had an overall composition of:

| boric acid | 5.0 pbw |
| corncob grit | 69.50 pbw |
| powdered sugar | 10.0 pbw |
| corn oil | 15.0 pbw |
| agar | 0.50 pbw |

The resulting shaped units could then be placed in bait stations for application.

EXAMPLE 3

Preparation of Granular Bait Using a Shaping Step

Granular bait was prepared using a wet method as described in Example 2 except gelatin was used in place of the agar. Gelatin commercially available from Becton Dickinson and Company (Sparks, Md.) under the trade designation Gelatin was used.

The resulting granules had an overall composition of:

| boric acid | 5.0 pbw |
| corncob grit | 69.50 pbw |
| powdered sugar | 10.0 pbw |
| corn oil | 15.0 pbw |
| gelatin | 0.50 pbw |

The resulting shaped units could then be placed in bait stations for application.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A granular bait comprising:
   (a) from about 0.5 to about 6.0 percent by weight of at least one pesticidally active ingredient selected from the group consisting of boric acid, orthoboric acid, sodium borates, sodium calcium borates, calcium borates, and combinations thereof:
   (b) from about 50 to about 90 percent by weight of one or more carrier materials, wherein at least one carrier material is corncob grit, or ground soy bean hulls;
   (c) at least 5 percent of a first attractant selected from the group consisting of powdered sugar, granulated sugar, dextrose, sucrose, fructose, sugar-containing food by-products containing at least 60 percent by weight sugar, or a combination thereof; and
   (d) a second attractant selected from the group consisting of corn oil, soy oil, vegetable oil, or oil-containing food by-products containing at least 10 percent by weight oil, or a combination thereof.

2. The granular bait of claim 1, wherein the at least one pesticidally active ingredient comprises boric acid or orthoboric acid.

3. The granular bait of claim 2, wherein the first attractant comprises powdered sugar.

4. The granular bait of claim 3, wherein the second attractant comprises corn oil.

5. The granular bait of claim 4, wherein the at least one carrier material is corncob grit.

6. The granular bait of claim 1, wherein the granular bait further comprises at least one additional carrier material selected from agar, gelatin, or a combination thereof.

7. The granular bait of claim 1, wherein the first attractant comprises powdered sugar having a particle size of 6× to 12×.

8. The granular bait of claim 1, wherein the bait comprises a plurality of particles, wherein the plurality of particles pass through a #8 mesh screen and do not pass through a #100 mesh screen.

9. The granular bait of claim 1, wherein the bait comprises a plurality of particles, wherein the plurality of particles pass through a #14 mesh screen and do not pass through a #80 mesh screen.

10. The granular bait of claim 1, wherein the bait comprises a plurality of particles, wherein each particle of the plurality of particles has a particle size ranging from about 160 μm to about 1100 μm.

11. The granular bait of claim 1, wherein the bait is substantially water-free.

12. A plurality of granular bait particles comprising the granular bait of claim 1.

13. The granular bait of claim 1, wherein the bait comprises:
 (a) from about 0.5 to about 6.0 percent by weight of boric acid or orthoboric acid;
 (b) from about 50 to about 90 percent by weight of corncob grit;
 (c) from about 5 to about 15 percent by weight of powdered sugar; and
 (d) from about 10 to about 20 percent by weight of corn oil;
 wherein all percents by weight are based on a total weight of the granular bait.

14. The granular bait of claim 1, wherein the bait consists essentially of:
 (a) from about 0.5 to about 6.0 percent by weight of boric acid or orthoboric acid;
 (b) from about 50 to about 90 percent by weight of corncob grit;
 (c) from about 5 to about 15 percent by weight of powdered sugar; and
 (d) from about 10 to about 20 percent by weight of corn oil;
 wherein all percents by weight are based on a total weight of the granular bait.

15. The granular bait of claim 1, wherein the bait consists essentially of:
 (a) boric acid or orthoboric acid;
 (b) corncob grit;
 (c) powdered sugar; and
 (d) corn oil.

16. The granular bait of claim 1, wherein the at least one pesticidally active ingredient comprises from about 4.0 to about 6.0 percent by weight of the bait.

17. A method of reducing insect pests in an area, wherein the method comprises:
 applying granular bait to at least a portion of the area, wherein the granular bait comprises the granular bait of claim 1.

18. A granular bait consisting of:
 (a) an effective amount of from about 5 percent by weight of at least one pesticidally active ingredient of boric acid, orthoboric acid, or mixtures thereof:
 (b) about 70 percent by weight corncob grit carrier;
 (c) about 10 percent by weight powdered sugar first attractant; and
 (d) about 15 percent by weight corn oil second attractant,
 wherein the percents by weight are based on the total weight of the granular bait.

* * * * *

UNITED STATES PATENT AND TRADEMARK OFFICE
CERTIFICATE OF CORRECTION

| | | |
|---|---|---|
| PATENT NO. | : 7,223,415 B1 | Page 1 of 1 |
| APPLICATION NO. | : 10/266191 | |
| DATED | : May 29, 2007 | |
| INVENTOR(S) | : Malone et al. | |

It is certified that error appears in the above-identified patent and that said Letters Patent is hereby corrected as shown below:

Column 3, Line 13
Delete the "," after "bait" and before "Desirably" and replace with a --.--

Column 3, Line 34
Delete the "," after "thereof" and replace with a --.--

Column 5, Line 37
Delete "there of" and replace with --thereof--

Signed and Sealed this

Thirtieth Day of October, 2007

JON W. DUDAS
*Director of the United States Patent and Trademark Office*